(12) United States Patent
Hoag

(10) Patent No.: US 8,798,979 B2
(45) Date of Patent: Aug. 5, 2014

(54) INFUSION DEVICE DATA SET ANALYZER

(75) Inventor: Robert E. Hoag, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 1520 days.

(21) Appl. No.: 11/433,812

(22) Filed: May 11, 2006

(65) Prior Publication Data

US 2006/0259327 A1 Nov. 16, 2006

Related U.S. Application Data

(60) Provisional application No. 60/680,096, filed on May 11, 2005.

(51) Int. Cl.
*G06G 7/48* (2006.01)
*G06G 7/58* (2006.01)
*G01N 33/48* (2006.01)
*G01N 31/00* (2006.01)

(52) U.S. Cl.
USPC ............ 703/11; 703/12; 702/19; 702/22

(58) Field of Classification Search
None
See application file for complete search history.

(56) References Cited

U.S. PATENT DOCUMENTS

| | | |
|---|---|---|
| 5,557,514 A | 9/1996 | Seare et al. |
| 5,681,285 A | 10/1997 | Ford et al. |
| 6,000,828 A | 12/1999 | Leet |
| 6,151,581 A | 11/2000 | Kraftson et al. |
| 6,269,340 B1 | 7/2001 | Ford et al. |
| 6,317,719 B1 | 11/2001 | Schrier et al. |
| 6,778,994 B2 | 8/2004 | Gogolak |
| 6,789,091 B2 | 9/2004 | Gogolak |
| 2003/0046110 A1 * | 3/2003 | Gogolak ........................... 705/2 |
| 2003/0144878 A1 | 7/2003 | Wilkes et al. |
| 2003/0144884 A1 | 7/2003 | Mayaud |
| 2004/0010511 A1 | 1/2004 | Gogolak |
| 2004/0073454 A1 | 4/2004 | Urquhart et al. |
| 2004/0117126 A1 | 6/2004 | Fetterman et al. |
| 2004/0122709 A1 | 6/2004 | Avinash et al. |
| 2004/0128162 A1 * | 7/2004 | Schlotterbeck et al. .......... 705/2 |
| 2004/0176985 A1 | 9/2004 | Lilly et al. |
| 2007/0214003 A1 * | 9/2007 | Holland et al. ................... 705/2 |

FOREIGN PATENT DOCUMENTS

| | | |
|---|---|---|
| EP | 1 433 456 | 6/2004 |
| JP | A-7-235895 | 9/1995 |
| JP | A-2002-261701 | 9/2002 |
| JP | A-2003-70852 | 3/2003 |
| WO | WO 02/069099 | 9/2002 |
| WO | WO 03/022327 | 3/2003 |
| WO | WO 03/024385 | 3/2003 |
| WO | 2004072828 A2 | 8/2004 |

OTHER PUBLICATIONS

Eskew J.A. et al., "Using innovative technologies to set new safety standards for the infusion of intravenous medications," Hospital Pharmacy, Nov. 1, 2002, pp. 1179-1189, vol. 37, No. 11, Lippincott, Philadelphia, U.S.

Office Action for JP Patent Application No. 2008-511459 dated Nov. 29, 2011 in 3 pages.

* cited by examiner

*Primary Examiner* — Larry D Riggs, II
(74) *Attorney, Agent, or Firm* — McDermott Will & Emery LLP

(57) ABSTRACT

A system and method for evaluating drug data sets is provided. The system and method includes identifying when entries in a current data set differ from a data set comprising an aggregate of entries for a plurality of institutions, and prompting a user to determine if a change in the current data set should be changed. The system and method also identifies cases where different dose units are used for the same drug. A report is generated noting exceptions.

21 Claims, 5 Drawing Sheets und States Patent No. US 8,798,979 B2

INFUSION DEVICE DATA SET ANALYZER

RELATED APPLICATIONS

This application claims the benefit of priority to U.S. Provisional Patent Application Ser. No. 60/680,096, filed May 11, 2005 entitled "Infusion Device Data Set Analyzer," the entirety of which is hereby incorporated herein.

FIELD OF THE INVENTION

The present invention relates generally to the administration of medications, and more particularly, to a system and a method for comparing drug administration data selected by a healthcare facility to drug administration data accumulated from another source or sources.

BACKGROUND OF THE INVENTION

The intravenous ("IV") infusion of medical fluids into patients is used in the treatment of many different diseases. Depending on the physician, the fluids are delivered to the patient by means of a surgically inserted, main-line catheter or at a peripheral site, such as the patient's arm or leg. Often, due to the patient's condition, it is critical that the prescribed medication dose be administered at the prescribed rates during the designated period of time.

Infusion pumps are often used to administer medications to a patient. The administration may be conducted in small discrete doses or may be given at an essentially continuous rate. Infusion pump therapy may be electronically controlled to deliver precise, metered doses at exactly determined levels, thereby providing a beneficial gradual infusion of medication to the patient. In this manner, the infusion pump is able to mimic the natural process whereby chemical balances are maintained precisely by operating on a continuous time basis.

Many drugs that can be administered by infusion pump and by other means have minimum doses, below which they may not be effective and maximum doses, above which patient harm could result. In many cases, the level of minimum dose and maximum dose depends upon the "Profile," that is, where the drug is used. For instance, a neonatal profile often has a much lower maximum dose of a drug than an ICU profile. Maximum and minimum doses, as well as many other drug administration parameters, are generated by the healthcare facility. These are data sets pertaining to the administration of drugs; i.e., drug data sets. It can be useful to a healthcare facility to compare the data set it uses for its drugs to data sets of other healthcare facilities to determine if it is comparable or if there are notable differences.

Modern infusion pumps and medication delivery systems include processors and memory and are capable of analyzing incoming or inputted values of operational parameters to determine if they are within the ranges of parameters stored in the above described data sets. Thus, each pump analyzes incoming infusion data and can alert a care giver where one or more of the incoming parameters falls outside of the hospital's or institution's accepted ranges for the parameter.

In setting up a hospital's drug administration data sets, pharmacy consultants analyze the hospital's drug data set for clinical appropriateness to determine whether the use of a particular drug in a hospital falls within recognized usage of the drug. For example, the consultant attempts to determine whether a drug is being used within a dosage range recognized as a best dosage range of the drug, and will identify situations where inappropriate dose ranges are being used for a particular type of patient.

This analysis is usually performed by comparing the healthcare facility's data set against a large printout of the compiled data sets of other healthcare facilities. This analysis usually takes about 4 to 5 hours, and is very tedious and prone to error. Hence those skilled in the art have recognized a need for a system and method that accomplishes the objectives of data set comparison on a faster and more accurate basis. The invention fulfills this need and others.

SUMMARY OF THE INVENTION

Generally, the system and method of the present invention includes comparing a healthcare facility's drug data set which is intended to be used in monitoring and controlling the delivery of medication to patients with a data set of similar information compiled from the drug data sets used by a plurality of other healthcare facilities, and identifying those items of the facility's drug data set that differ in some significant manner from the aggregate data of the compiled data set. Such a comparison can include comparing profile names, drug names, units associated with delivery of the drug, limits associated with the delivery of the drugs, such as dosage or rate of delivery limits, and other parameters as identified by the healthcare facility.

In one aspect, the system and method of the present invention includes a system for analyzing a drug data set for clinical appropriateness, comprising: an input device for inputting a first drug data set to be analyzed, the first drug data set having a plurality of drugs and associated with each drug, a plurality of data elements comprising data relevant to administration of the drug to patients, the data elements including dosing information; a memory having an established drug data set, the established drug data set having a plurality of drugs and associated with each drug, a plurality of data elements comprising data relevant to administration of the drug to patients, the data elements including dosing information; a processor connected with the memory to receive the established drug data set and connected to the input device to receive the first drug data set, the processor programmed to compare the first drug data set against the established drug data set, the comparison including identifying matches between the drugs of the first drug data set with the drugs of the established drug data set and comparing the dosing information of any identified matches; and a reporting device connected with the processor to report the results of the comparison.

In another aspect, the processor is also programmed to identify a drug contained in the first drug data set that is not contained in the established drug data set; and the reporting device also reports such unmatched drug as an exception. In still another aspect, the processor is programmed to identify differing dosing units used for the drugs contained in the first drug data set that are not used for the same drugs in the established drug data set; and the reporting device also reports such dosing unit's difference.

In yet another aspect, the system of the present invention prompts a user to change the dosing units of a drug contained in the first drug data set upon report of differing dosing units used for the same drug contained in the established drug data set. In still another aspect, the processor is also programmed to automatically convert the dosing units of a drug in the first drug data set to the dosing units of the same drug in the established drug data set prior to the comparison by the processor, and in a further aspect, the processor is also programmed to identify differing dosing limits used for each of the drugs contained in the first drug data set that are not used for same drugs in the established drug data set; and the reporting device also reports such dosing limits difference. In an alternative aspect, the system prompts a user to change the dosing limits of a drug contained in the first drug data set upon report of differing dosing limits used for the same drug contained in the established drug data set.

In a further aspect, the processor is also programmed to automatically convert the dosing limits of a drug in the first drug data set to the dosing limits of the-same drug in the established drug data set prior to comparison by the processor. In a still further aspect, the memory has a plurality of established drug data sets; the processor is connected to the memory to receive the plurality of established drug data sets; and the processor is programmed to compare the first drug data set against the plurality of established drug data sets. In an even further aspect, the processor is also programmed to identify differing dosing units for a drug contained in the first drug data set if less than two established drug data sets utilize the same dosing units for the same drug; and the reporting device also reports such dosing unit's difference as an "exception."

In yet another aspect, the processor is also programmed to identify the number of differing dosing limits used for each of the drugs contained in the first drug data set that are not used for each of the same drugs in the plurality of established drug data sets; and the reporting device also reports such number. In an alternative aspect, the processor is programmed to determine an acceptable variance range of minimum and maximum dosing limits for any drug found among the plurality of established drug data sets. In yet another alternative aspect, the processor is programmed to identify a minimum dosing limit of a drug contained in the first drug data set falling outside the acceptable variance range; and the reporting device also reports such identification. In still another aspect, the processor is programmed to identify a maximum dosing limit of a drug contained in the first drug data set falling outside the acceptable variance range; and the reporting device also reports such identification.

In still another aspect of the system and method of the present the established drug data set represents a data set generated by a medical care facility, and alternatively, each of the plurality of established drug data sets represents a data set generated by different medical care facilities.

In yet another aspect, the system in accordance with principles of the system and method of the present invention is part of an editor program used to create a drug data set.

In still another aspect, system of the present invention may be housed on a portable computing device. In yet another aspect, the first drug data set is housed on a first device and the established drug data set and the processor is housed on a second device.

In a further aspect, the present invention includes a computerized method for analyzing a drug data set for clinical appropriateness, comprising: receiving a first drug data set to be analyzed, the first drug data set having a plurality of drugs and associated with each drug, a plurality of data elements comprising data relevant to administration of the drug to patients by an infusion pump, the data elements including infusion dosing information; maintaining a reference data base having an established drug data set, the established drug data set having a plurality of drugs and associated with each drug, a plurality of data elements relevant to administration of the drug to patients by an infusion pump, the data elements including infusion dosing information; comparing the first drug data set against the established drug data set, the comparing including identifying matches between the drugs of the first drug data set with the drugs of the established drug data set and comparing the infusion dosing information of any identified matches; and reporting the results of the comparison. In an alternative aspect, maintaining a reference data base comprises maintaining a reference data base having a plurality of established drug data sets.

Other features and advantages of the invention will become apparent from the following detailed description, taken in conjunction with the accompanying drawings, which illustrate, by way of example, the features of the invention.

DETAILED DESCRIPTION OF PREFERRED EMBODIMENTS

The subject invention is directed to a system and method for automating a comparison of the drug data set of a specific drug library, including the associated limits, with compiled historical data of data sets from libraries created by other healthcare facilities.

Figure 1:
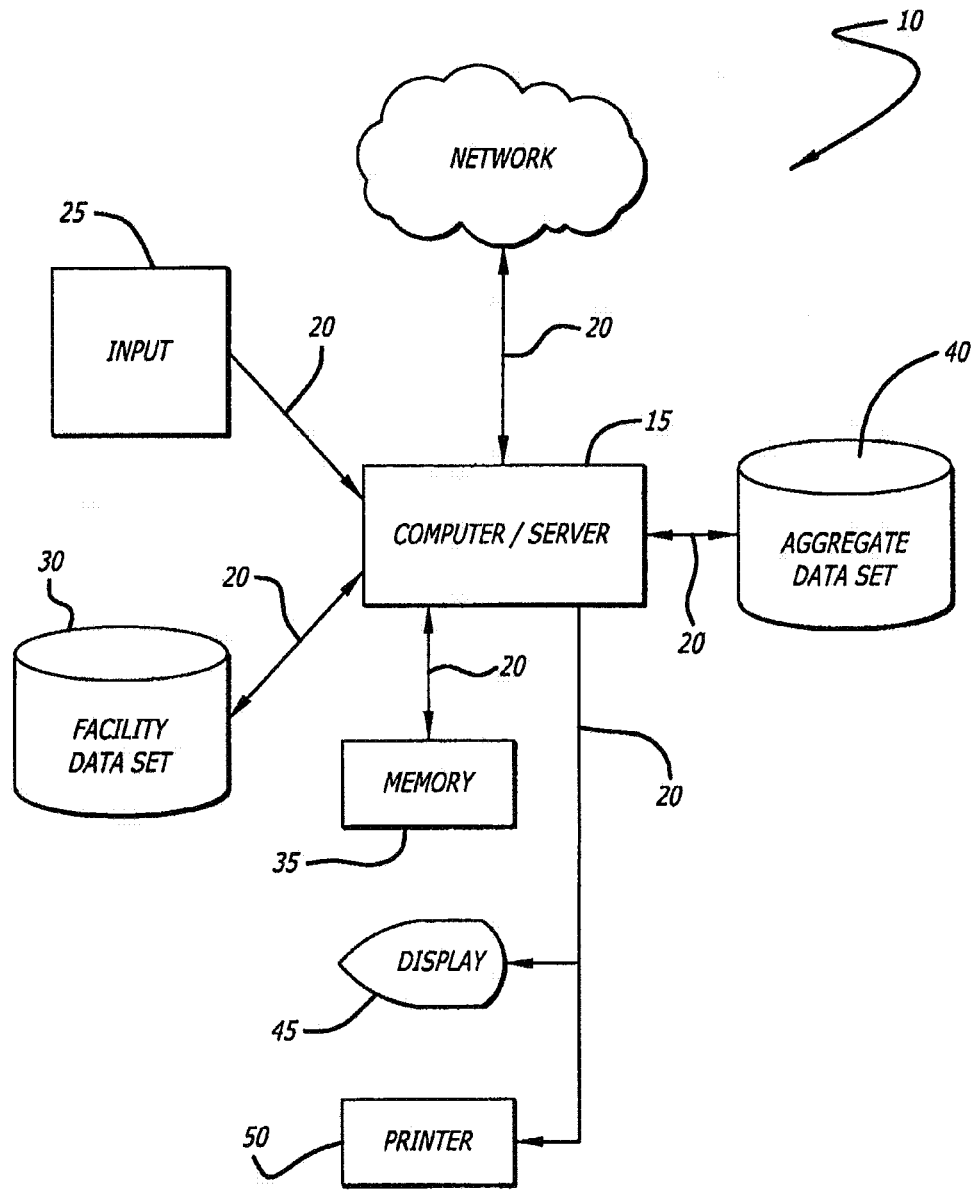
FIG. 1 is graphical representation illustrating one embodiment of the present invention.

Referring now to the drawings in detail, in which like reference numerals indicate like or corresponding elements among the several figures, there is shown in FIG. 1 a graphical representation of a system 10 embodying principles of the present invention. System 10 includes a computer/server 15 that is programmed using appropriate computer programming commands to carry out specific tasks desired by the program designer. In this instance, the computer/server 15 will be programmed using software that is designed to carry out the comparison, identification and reporting tasks set forth in more detail below.

Computer/server 15 is in operable communication with a variety of peripheral accessories, which may be contained within the same physical case or location as the computer/server 15, or which may be located remote from computer/server 15. Communication between the computer/server 15 and the various peripheral accessories is carried out using suitable communication busses and/or wired or wireless communication means 20, such as direct wiring, Ethernet, LAN or internet connections, as are known by those skilled in the art. Moreover, the entire system may be in communication with another system, so that comparison of the data sets may be carried out at a location remote from the healthcare facility.

Typically, peripheral accessories may include, but are not limited to, for example, an input means 25, a means for accessing an institutional database 30, a memory 35, a data base 40 of aggregated data compiled from other healthcare facilities, a display 45 and a printer 50. Those skilled in the art will understand other accessories, servers, processors or computers and clinical devices may also be in communication with computer/server 15, and may be used to carry out aspects of the method of the present invention. The processor of computer/server 15 may use memory 35 to contain application or operating programs used to program the processor to carry out general and specific tasks. Moreover, memory 35 may be used by the processor of computer/server 15 as a resource when comparing the facility's data set 30 to the aggregate data set 40. Such processes are well known to those skilled in the art.

Drug data sets are assembled at a healthcare facility for use in monitoring the delivery of medication to a patient. Often, these drug data sets are loaded into an appropriately configured infusion pump, and are used as a standard for comparison during entry of infusion data parameters into the pump to operate the pump. Such entry may either be accomplished manually by a care giver, or through communication between the pump and a healthcare facility's information network.

The drug data sets must include entries for all of the drugs used in the healthcare facility. Additionally, it is important to understand that drugs are not used in the same dosages, or delivered in the same manner or at the same rate in all areas of a healthcare facility. For example, a drug used in an emergency room setting for treatment of adults is often used in quite different dosages than when the same drug is used in a neonatal care setting.

Given the large number of entries in such a drug data set, many healthcare facilities, in an ongoing attempt to improve medication delivery to their patients, desire to compare drug usage in their facilities with the usage in other facilities. The concept is to develop a drug data set that is consistent with a consensus usage of the drug.

To accomplish this comparison, drug data sets have been collected from a large number of healthcare facilities across the United States and all of that data has been assembled in a drug-by-drug data base. The drugs are organized by the generic name of the drug and by manufacturers' names. In some cases, drugs have multiple different names (e.g., acetaminophen, Tylenol, a trademark of McNeil Pharmaceutical). The data base may also be arranged using a variety of other criteria, such a treatment area or profile.

Healthcare facilities typically generate their own data sets, which may be quite large. Since it is a major project to alter the contents of the data sets once the data sets are uploaded into the facility's infusion pumps, healthcare facilities desire a "reasonableness check" of the data set before it is approved and uploaded to the infusion pumps.

In accordance with one embodiment of the present invention, the system and method perform a line-by-line comparison of the healthcare facility's data set to a data set compiled from aggregated data collected from a plurality of healthcare facilities. Generally, the facilities compare dosing units, dosing limits, pump limits, and other drug administration parameters to the accumulated data from the numerous other healthcare facilities. Such a comparison, if done manually, would typically take four or more hours; however, with the system and method of the invention, it takes only minutes to perform the comparison and print a report. The report typically indicates, for example, whether the present healthcare facility's drug data set is the same as or is different from the other healthcare facilities whose data was compiled One important aspect of the present invention is that it identifies whether the range of parameter's used for a drug in the healthcare facility appears reasonable in view of the use of that drug by other facilities, and attempts, where there is sufficient data, to provide an indication of that reasonableness. For example, in one embodiment of the invention, the system and method compare the usage of the drug and then indicates whether the usage of the drug falls within a 95% confidence interval of use of that drug (for a specific profile) by other facilities. In other words, if there is enough data to make a reasonable comparison, a determination is made whether the current usage falls with two standard deviations of the distribution of usage by other facilities.

In another embodiment, the system and method of the present invention also identifies whether the present healthcare facility is using units of measure that differ from other healthcare facilities. Where differences are found, the system and method identifies the differences, and prompts for a care giver to accept or change the units.

In carrying out various embodiments of the present invention, the computer/server 15 is instructed by appropriate programming code to compare information from the present healthcare facility to information stored in the aggregate data set or data base 40 compiled from drug data sets retrieved from a plurality of healthcare facilities. This process may be carried out in a number of manners. For example, while time consuming and not normally preferred, drug information to be compared may be manually entered using input means 25. Usually, however, computer/server 15 will be provided access to the healthcare facilities drug data set 30, and will draw data from data set 30 as it carries out its instructions. In this manner, the process may be automated, and may be accomplished in a few minutes, rather than the hours a manual process typically requires.

Figure 2A:
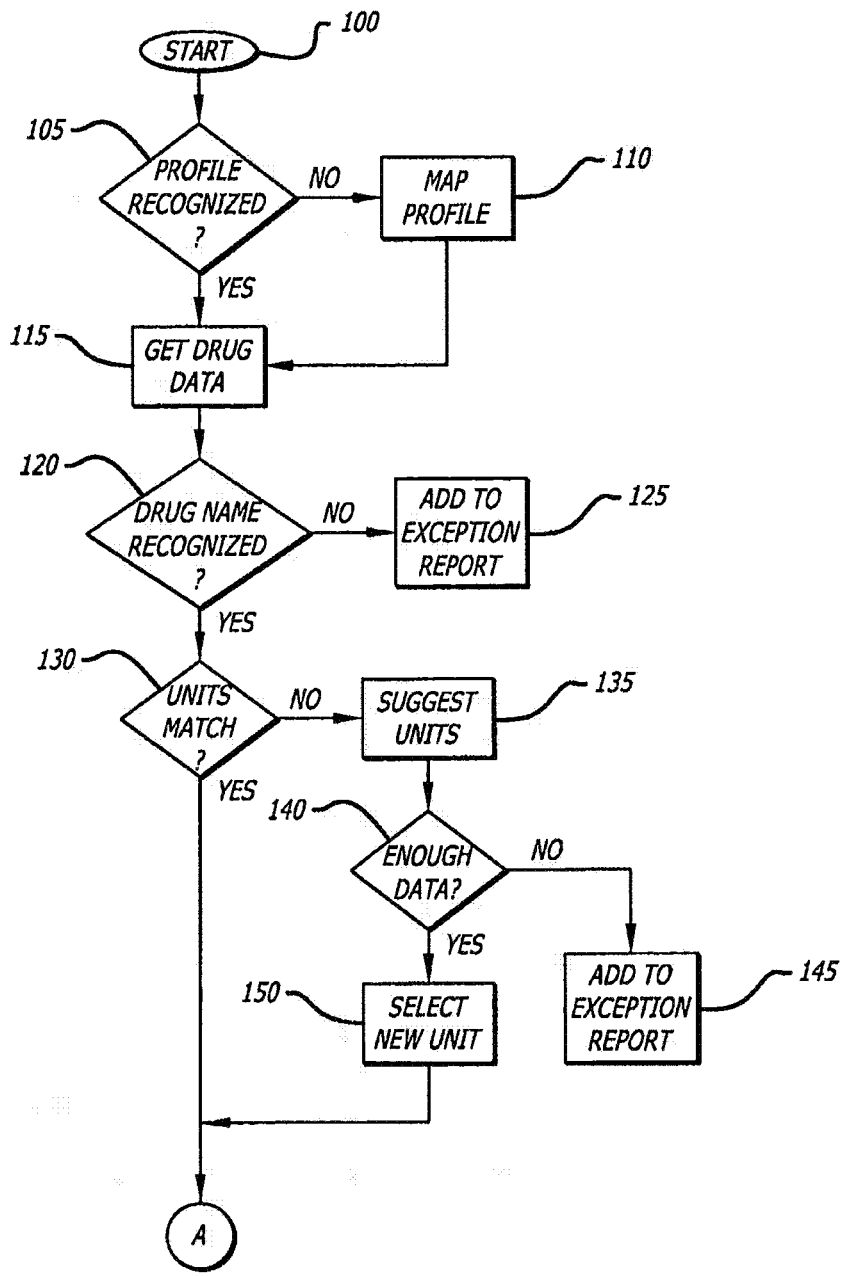
FIGS. 2A and 2B are block diagrams illustrating a method in accordance with one embodiment of the present invention.
Figure 2B:
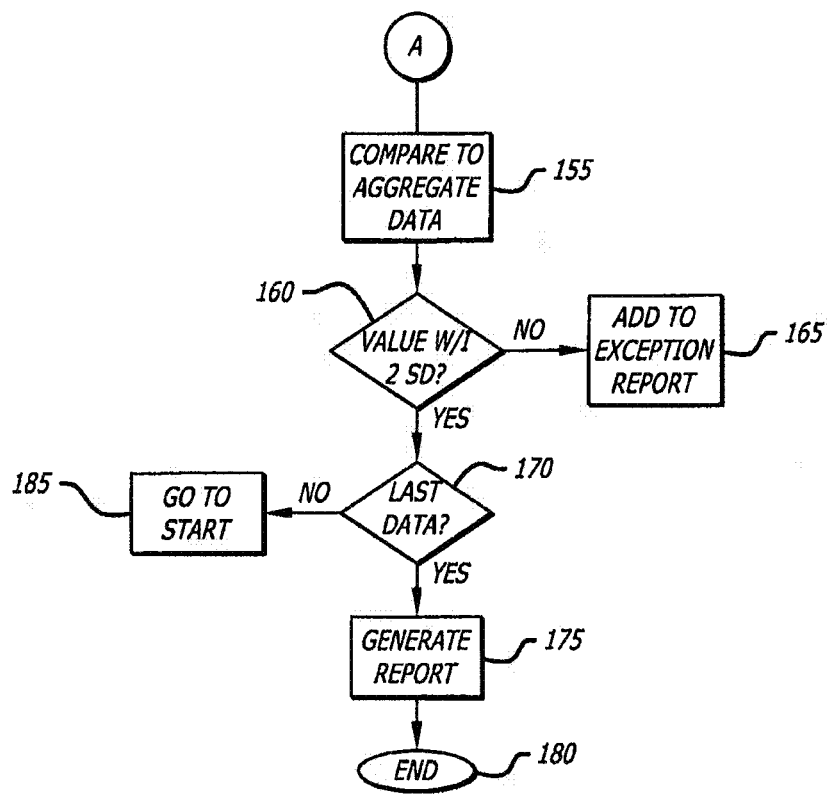
Figure 3:
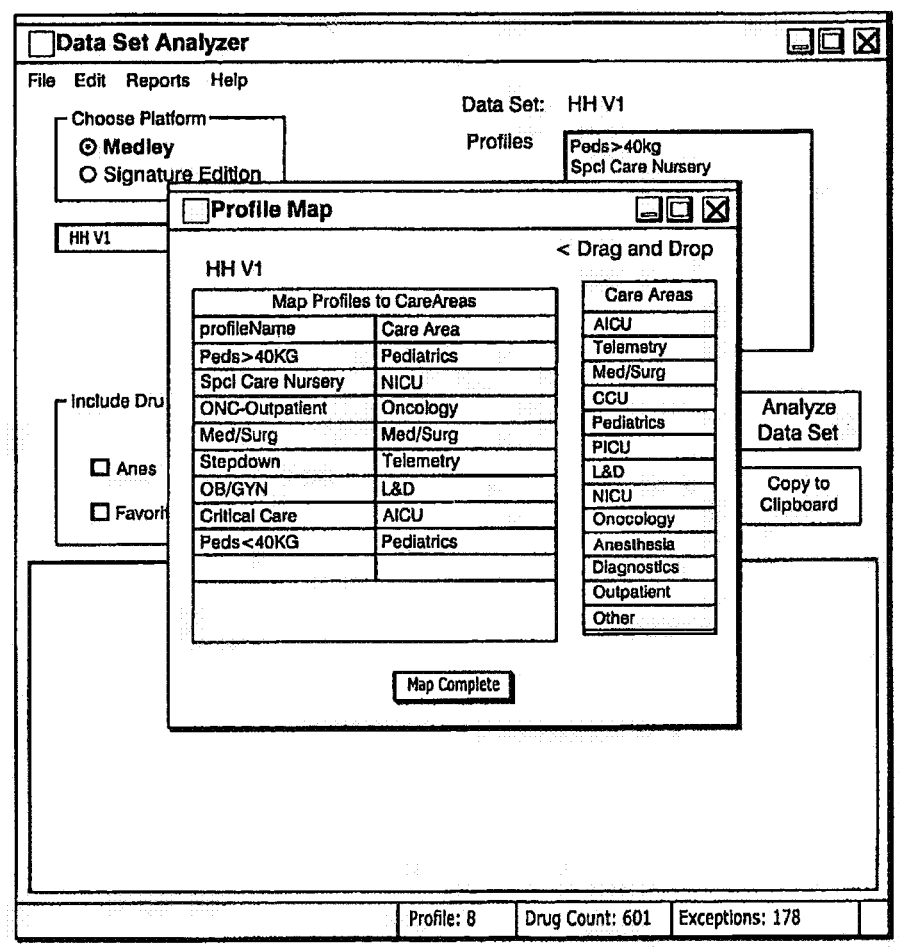
FIG. 3 is a graphical representation of a display screen presented to a user providing for mapping a profile name used by a facility to profiles contained in an aggregate data set.

FIG. 2 is a block diagram illustrating one embodiment of the method of the present invention that accomplishes the comparison of a healthcare facilities drug data set with a data set containing aggregated drug data compiled from a plurality of healthcare facilities. In this embodiment, the method begins at "start" identified by reference numeral 100. The method first determines if the profile name used by the healthcare facility matches the names of profiles stored in the aggregate data base in box 105. If the profile name is not recognized, the program running on the computer/server 15 may cause a window, such as that illustrated in FIG. 3, to open and prompt the a user to map the profile name used by the facility to a profile name contained within the aggregate database. This mapping is carried out in box 110 of FIG. 2.

Once the profile has been mapped, if necessary, the program then retrieves data from the healthcare facility's data set in box 115. The program then determines whether the drug name used in the healthcare facility's data set is recognized, that is, does it exist in the aggregate data set, in box 120. If the drug name is not recognized, the drug name is added to an exception report in 125. Those skilled in the art will understand that this name may be displayed, printed immediately, or temporarily stored in a memory or buffer for latter display or printing.

Figure 4:
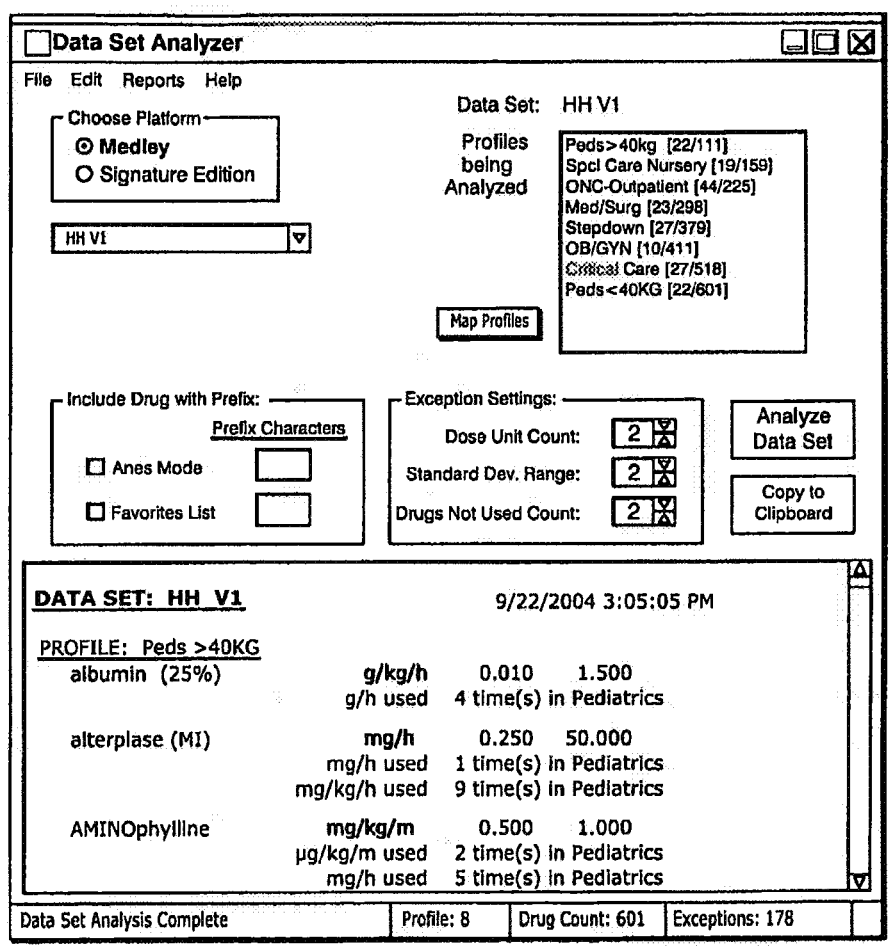
FIG. 4 is a graphical representation of a display screen illustrating the display of values indicated as exceptions, along with possible alternative values that could be used, and the frequency of their use by other facilities.

If the drug name is recognized by the program in box 120, the program then analyzes the units used by the healthcare facility for the drug, and determines whether those units match the units associated with the entries for the drug contained in the aggregate data set in box 130. If the units do not match, the program branches to box 135, where the program may display a screen to the user, such as that illustrated in FIG. 4, identifying the drug name, the units used by the facility, and also display the frequency those units, and alternative units, are used by facilities whose drug data is contained in the aggregate data set. For example, as shown in FIG. 4, the facility uses mg/h for alteplase (MI) in its Peds>40 KG profile. The program displays data showing that such a unit is used by only one other facility, while nine facilities use mg/kg/h for units. The system then prompts the user to change the units in box 150, if there is enough data to make a reasonable selection, as determined in box 140. If there is not enough data to make a reasonable determination, the drug name and units used is added to the exception report.

The determination of reasonableness of a drug name or unit is made in accordance with criteria which may be selected by the healthcare facility as having particular significance. For example, if the system finds that less than two other healthcare facilities use the units that the present healthcare facility uses, those units may be labeled as called an "exception." Similarly, the system may indicate than a certain number of other healthcare facilities use the dose (or other) limit of a certain number while the present healthcare facility uses the following identified dose limit, and that dose limit is used in only a small number of healthcare facilities. The comparison of the present healthcare facility's drug data set to the drug data sets of other healthcare facilities may be in percentage, it may be a straight number comparison, or it may be some other comparative value. For example, the comparison result may be of the type such as "The maximum dose for (drug) used in 75% of other healthcare facilities is the following limit XXXXX; but you use YYYYY which is used in only 3% of other healthcare facilities. Do you want to change?"

The program resumes at box 155 (FIG. 2B) where the parameter values of delivery of the drug, such as maximum and minimum dosage, rate of delivery, concentration or other delivery parameter, are compared to similar parameters contained within the aggregate data base or set. This comparison can be configured, as illustrated by box 160, to apply some reasonable limit within with the used value should fall. In this embodiment, for example, the healthcare facility has selected a range of two standard deviations from the mean value contained within the aggregate data base as an acceptable range of values. If the facility's value falls beyond two standard deviations, the value is added to the exception report in box 165.

At this point, several alternative embodiments of the process are possible. For example, when a value is identified as falling out side of the acceptable range established by the healthcare facility, the program may display the drug name and value, and ask the user if he or she wants to change the value. Such a change would update the facilities data set with the new value. A log of such changes may also be maintained, which could be printed as a report at a latter time to qualify the changes to the data set if necessary. Alternatively, all changes to the data set may be made at a later time, once a comprehensive report of all of the identified exceptions found in the facilities data set is generated.

In the illustrated embodiment, after the comparison and determination steps of boxes 155 and 160 are completed, the program determines whether there is any further data to be processed in box 170. If there is more data to be processed, the program branches to box 185, which returns the program to the "start", or some other appropriate starting place in the program to continue processing the data in the facility's drug data set. If there is no more data to process, the program may branch to box 175, where a report set out the exceptions identified during the process for further review and correction. When the report is generated, the program ends at box 180.

The system and method in accordance with aspects of the invention described above automates the task of analyzing a facilities drug data set. In an automated way it looks for drug names that have been used by other healthcare facilities in a given Profile, and then compares drug library settings to the data base of all other healthcare facilities included in that data base. As will be understood by those skilled in the art, various processes may be applied to drug names, profile names, and parameters to ensure that the system and method of the present invention can accomplish the desired comparison. For example, if a drug name used by the facility cannot be found in the aggregate data set, the process may strip out unnecessary characters and re-compares the stripped-down drug name to find a match.

In addition to the situations described above, it is contemplated that an exception report may be created for a wide variety of cases, such as, for example, but not limited to, the following:

1. No drug name match. There is no history on this drug. The system and method then lists the drug entry. All non-alpha characters preceding the name will be stripped for comparison with the majority data. In one embodiment, for example, an "A" for anesthesia, or an "F" for favorite may then be displayed to the left of the drug name.

2. Dosing units were used once or fewer times. In this case, the program embodying the method of the present invention may list the drug entry with the dosing units in BOLD. This is then followed by dosing units that have been used by other facilities for comparison, followed by the frequency of their use.

3. The minimum drug limit is outside two standard deviations. In this case, the system may display the minimum value in BOLD and display the accepted range, for example, two standard deviations, for comparison.

4. The maximum drug limit is outside two standard deviations. In this case, the system may display the maximum value in BOLD and display the accepted range, for example, two standard deviations, for comparison.

The invention provides a convenient way of accessing data sets without opening and applying a complex computer analysis program, allows analysis of a complex data set in an automated way. The system and method of the present invention may include analysis of a wide range of parameters, such as, for example, bolus dosing, hard limit comparison, and configurations settings, as well as cross-profile comparison of dosing units. The exception report generated by the various embodiments of the system and method of the present invention may include outputting the exception report to a wide variety of application programs, such as Excel, Word (both of which are distributed by Microsoft, Inc.), and other appropriate applications. In this manner, the system and method of the present invention provides an accurate speedy way to analyze a healthcare facility's drug data set to ensure against inaccuracies. It also provides a method of comparing the complex drug data set to data collected from a plurality of other healthcare facilities. This ensures that a healthcare facility is using a drug in a manner consistent with the majority of other users, which may provide benefits of more consistent and effective treatment of the facilities patients.

While several particular forms of the invention have been illustrated and described, it will be apparent that various modifications can be made without departing from the spirit and scope of the invention.

What is claimed is:

1. A system for reporting clinical appropriateness of a drug data set, comprising:
    an input device for inputting a first drug data set to be analyzed, the first drug data set having a plurality of drugs and associated with each drug, a plurality of data elements comprising data relevant to administration of the drug to patients, the data elements including dosing information;
    a memory having an established drug data set, the established drug data set having a plurality of drugs and associated with each drug, a plurality of data elements comprising data relevant to administration of the drug to patients, the data elements including dosing information;
    a processor connected with the memory to receive the established drug data set and connected to the input device to receive the first drug data set, the processor programmed to compare the first drug data set against the established drug data set, the first drug data set comprising drug usage information of a healthcare facility and the established drug data set comprising drug usage information of a plurality of other healthcare facilities; and a reporting device connected with the processor to report the results of the comparison to a user.

2. The system of claim 1 wherein:
the processor is also programmed to identify a drug contained in the first drug data set that is not contained in the established drug data set; and
the reporting device also reports such unmatched drug as an exception.

3. The system of claim 1 wherein:
the processor is also programmed to identify differing dosing units used for the drugs contained in the first drug data set that are not used for the same drugs in the established drug data set; and
the reporting device also reports such dosing unit's difference.

4. The system of claim 1 wherein the system prompts a user to change the dosing units of a drug contained in the first drug data set upon report of differing dosing units used for the same drug contained in the established drug data set.

5. The system of claim 3 wherein the processor is also programmed to automatically convert the dosing units of a drug in the first drug data set to the dosing units of the same drug in the established drug data set prior to the comparison by the processor.

6. The system of claim 1 wherein:
the processor is also programmed to identify differing dosing limits used for each of the drugs contained in the first drug data set that are not used for same drugs in the established drug data set; and
the reporting device also reports such dosing limits difference.

7. The system of claim 1 wherein the system prompts a user to change the dosing limits of a drug contained in the first drug data set upon report of differing dosing limits used for the same drug contained in the established drug data set.

8. The system of claim 1 wherein:
the processor is also programmed to automatically convert the dosing limits of a drug in the first drug data set to the dosing limits of the same drug in the established drug data set prior to comparison by the processor.

9. The system of claim 1 wherein:
the memory has a plurality of established drug data sets;
the processor is connected to the memory to receive the plurality of established drug data sets; and
the processor is programmed to compare the first drug data set against the plurality of established drug data sets.

10. The system of claim 9 wherein:
the processor is also programmed to identify differing dosing units for a drug contained in the first drug data set if less than two established drug data sets utilize the same dosing units for the same drug; and
the reporting device also reports such dosing unit's difference as an "exception."

11. The system of claim 9 wherein:
the processor is also programmed to identify the number of differing dosing limits used for each of the drugs contained in the first drug data set that are not used for each of the same drugs in the plurality of established drug data sets; and
the reporting device also reports such number.

12. The system of claim 9 wherein the processor is programmed to determine a variance range of minimum and maximum dosing limits for any drug found among the plurality of established drug data sets.

13. The system of claim 12 wherein:
the processor is programmed to identify a minimum dosing limit of a drug contained in the first drug data set falling outside the acceptable variance range; and
the reporting device also reports the identification of the maximum closing limit.

14. The system of claim 12 wherein:
the processor is programmed to identify a maximum dosing limit of a drug contained in the first drug data set falling outside the acceptable variance range; and
the reporting device also reports the identification of the maximum closing limit.

15. The system of claim 1 wherein the established drug data set represents a data set generated by a medical care facility.

16. The system of claim 9 wherein each of the plurality of established drug data sets represents a data set generated by different medical care facilities.

17. The system of claim 1 wherein the system is part of an editor program used to create a drug data set.

18. The system of claim 1 wherein the system is housed on a portable computing device.

19. The system of claim 1 wherein the first drug data set is housed on a first device and the established drug data set and the processor are housed on a second device.

20. The system of claim 1, the comparison including identifying matches between the drugs of the first drug data set with the drugs of the established drug data set and comparing the dosing information of any identified matches.

21. The system of claim 1, the comparison including determining whether usage information for a drug in the first drug data set is within a predetermined confidence interval of the drug in the established drug data set.

* * * * *